United States Patent [19]

Revel et al.

[11] Patent Number: 5,541,312
[45] Date of Patent: Jul. 30, 1996

[54] PRODUCTION OF INTERFERON

[75] Inventors: Michel Revel, Rehovot, Israel; Pierre Tiollais, Paris, France

[73] Assignee: Yeda Research & Development Co. Ltd., Rehovot, Israel

[21] Appl. No.: 425,934

[22] Filed: Sep. 28, 1982

Related U.S. Application Data

[62] Division of Ser. No. 208,925, Nov. 20, 1980, Pat. No. 5,468,607.

[30] Foreign Application Priority Data

Nov. 21, 1979 [IL] Israel .......................................... 58765

[51] Int. Cl.$^6$ .................................................. C12N 15/22
[52] U.S. Cl. ..................................... 536/23.52; 435/252.3; 435/385.1; 935/13
[58] Field of Search ........................... 435/68, 70, 91, 435/172, 253, 317, 69.51, 91.1, 172.3, 320.1, 252.3–252.35, 811; 536/27, 23.52; 935/13, 21; 530/351

[56] References Cited

U.S. PATENT DOCUMENTS

| | | | |
|---|---|---|---|
| 4,262,090 | 4/1981 | Colby et al. | 435/68 |
| 4,377,224 | 3/1983 | Cohen et al. | 435/172.3 |
| 5,326,859 | 7/1994 | Sugano et al. | 536/23.52 |

FOREIGN PATENT DOCUMENTS

| | | |
|---|---|---|
| 0041767 | 12/1981 | European Pat. Off. . |
| 0041313 | 12/1981 | European Pat. Off. . |

OTHER PUBLICATIONS

Kwan et al., Proc. Natl. Acad. Sci. USA 74, 178 (1977).
Burke, "The Interferon System: A Current Review to 1978", Baron et al (ed.), Texas Reports on Biology and Medicine, University of Texas Medical Branch, Galveston, TX, vol. 35, pp. 11–14, (1977).
Handbook of Biochemistry, Selected Data for Molecular Biology, 2nd Edition, Sober et al (ed.), Chemical Rubber Co., Cleveland, OH (1970), pp. H–104 and H–113 (compiled by H. S. Shapiro).
Taniguchi et al., *Proc. Japan Acad. Sci.*, 55 (B), 464 (1979).
Willing et al., *Nature*, 277, 534 (1979).
Research Disclosure, Jul. 1979 (anonymous).
Knight, E., et al., "Human Fibroblast Interferon: Amino Acid Analysis and Amino Terminal Amino Acid Sequence", (1980), *Science*, vol. 207, pp. 525–526.
Weissenbach, J., et al., "Identification of the Translation Products of Human Fibroblast Interferon mRNA in Reticulocytes Lysates", *Eur. J. Biochem.*, vol. 98, pp. 1–8, 1979.
Roberts, T. M., et al., "A General Method for Maximizing the Expression of a Cloned Gene", *PNAS*, vol. 76, No. 2, pp. 760–764, Feb. 1979.

(List continued on next page.)

*Primary Examiner*—James Martinell
*Attorney, Agent, or Firm*—Browdy & Neimark

[57] ABSTRACT

The present invention relates to a process to isolate genetic material (DNA) containing the nucleotide sequence coding for interferon in human fibroblastic cells which comprises cultivating cells producing interferon when exposed to an inducer of interferon, exposing same to such inducer, extracting messenger RNA from said induced cells, purifying the interferon messenger RNA, transcribing the messenger RNA into DNA and cloning the DNA in a suitable vector. Preferred cells are human diploid foreskin cells. The invention further relates to a process for engineering a bacterial strain to produce interferon polypeptide which comprises introducing a cloned interferon DNA into a suitable vector-carrier. A preferred vector-carrier is *E. coli*. The invention also relates to the mRNA of human interferon in highly purified form, to the mRNA of human interferon in β1 highly purified form, to the mRNA of human interferon in ⊕2 highly purified form, to the DNA coding for a polypeptide having interferon activity, insertable in a vector, such as plasmid pBR322, and also to human interferon β1 in highly purified form, and human interferon β2 in highly purified form.

7 Claims, 6 Drawing Sheets

OTHER PUBLICATIONS

Weiss et al., *Proc. Natl. Acad. Sci., USA,* 58:1104 (1967).
Green et al., *Cell Shape and Surface Architecture,* 1977, Alan R. Liss, Inc., New York, pp. 493–500, reprinted in *Readings in Mammalian Cell Culture* (second ed.), 1981, Pollack (ed.), Cold Spring Harbor Laboratory, Cold Spring Harbor, NY, pp. 149–156.

Lewin: *Gene Expression,* vol. 2, John Wiley & Sons, New York, 1974, pp. 148–151.
Cavalieri et al: Proc. Natl. Acad. Sci. USA 74, 4415 (1977).
St. John et al: Chem. Abstr. 90, 164536p (1979) of Cell 16, 443 (1979).
Williams et al: Chem. Abstr. 90, 182967j (1979) of J. Mol. Biol. 129, 19 (1979).

PRODUCTION OF INTERFERON

This is a division of application Ser. No. 208,925 filed Nov. 20, 1980, now U.S. Pat. No. 5,468,607.

BACKGROUND OF THE INVENTION:

Interferon is an important antiviral and antitumor protein produced by the body. Because of its species specificity, clinical use of interferon requires human interferon. The limited amount of interferon that can be produced from tissue culture cells or from fresh white blood cells, is not sufficient for large-scale clinical use. Introduction of the genetic information for human interferon into a bacterial microorganism could possibly, if it were available, allow the mass-production of a polypeptide having interferon activity. It is known that such techniques have been developed for human growth hormone and insulin.

The two types of interferon, i.e. leucocytes (IFN-α) and fibrobloast types (IFN-β) appear to be coded by different messenger RNAs (Cavallieri et al., 1977, Proc. Natl. Acad. Sci. U.S.A. 74, 4415–19). Isolation of these mRNAs in pure form has not been achieved as yet. This appears to be all the more difficult as the host cell is liable of synthesizing the interferon mRNA only as a result of exposure of the latter to suitable exogenous factors, for instance, viral infection or particular experimental polynucleotides such as poly (rI:rC), and only in minute amounts. Accordingly, if it had already been suggested to use a mRNA extract of host cells which had preliminarily been induced to produce interferon and to cause it to be translated in vitro in a cell-free system comprising all ingredients, particularly the natural aminoacids, whereby a protein preparation having interferon activity had been obtained, the interferon mRNA was indeed but a very minor proportion of the mRNAs being translated and accordingly the final protein preparation having interferon activity was more than highly contaminated with other proteins.

Therefore, the use of the mRNA preparations of the prior art as a starting material for direct transforming into double stranded DNA liable of being cloned after its insertion in a suitable vector, would involve screening difficulties which would be insuperable in practice.

OBJECTS OF THE INVENTION:

A major object of the present invention is to overcome to the greatest extent the above difficulties, particularly of providing a method of isolating the mRNA translatable into interferon, more particularly of human origin as well as the corresponding DNAs.

It is a further object of the present invention to provide a process for the isolation of genetic material (DNA) containing the nucleotide sequences coding for interferon in human cells.

It is yet a further object of the present invention to provide a process of this type wherein the messenger RNA is transcribed into DNA and which comprises cloning the DNA in a suitable vector. A preferred vector is a plasmid, and a preferred plasmid is a plasmid of the pBR322 type.

Furthermore it is an object of the present invention to provide a process to detect the different genetic sequence expressed in human cells when it is induced to produce interferon. A preferred embodiments comprises effecting a differential hybridization of the bacterial clones first with DNA from induced-cells RNA and second with identical DNA derived from uninduced-cell RNA.

It is yet a further object of the present invention to provide a process of engineering a bacterial strain to produce interferon polypeptide which comprises introducing a cloned interferon DNA into a suitable vector-carrier. The cloned interferon DNA is advantageously produced as set out above. A preferred vector is *E. coli* or another suitable microorganism. Another type of preferred vector-carrier is a eukaryotic cell.

Other and further objects of the present invention will become apparent hereinafter.

SUMMARY OF THE INVENTION

A preferred aspect of the present invention comprises a process to isolate genetic material (DNA) containing the nucleotide sequence coding for interferon in human cells, preferably fibroblastic cells, which comprises cultivating cells producing interferon when exposed to an inducer of interferon, exposing same to such inducer, extracting messenger RNA from said induced cells, purifying the interferon messenger RNA, reverse transcribing the messenger RNA into DNA and cloning the DNA in a suitable vector. According to a preferred embodiment the cells are human diploid foreskin cells. According to a preferred embodiment the inducer is double-stranded RNA.

The process according to the invention of enrichment of interferon mRNA or of a mRNA (inducible mRNA) of other protein or polypeptide the production of which is liable of being induced in the host cell by exogenous factors comprises:

a) exposing a culture of the host cell to such exogenous factor to induce in said host cells the synthesis of the said inducible mRNA;

b) extracting the mRNAs including the inducible mRNA formed in said induced cell culture therefrom as well as the mRNAs of a non-induced control culture of the same host cells;

c) synthesizing cDNA probes of the mRNAs of both the induced culture and the non-induced control culture using the corresponding mRNAs as templates (induced cDNAs and non-induced cDNAs);

d) synthesizing double-stranded cDNAs derived from the mRNA extracted from the induced culture, inserting said cDNAs in appropriate vectors, transfecting suitable microorganisms with the modified vectors obtained and cultivating said microorganisms under conditions suitable to cause selective development of microorganism colonies of said modified vectors (initial colonies);

e) forming duplicate colonies of said initial colonies;

f) causing freeing in situ of the DNAs of both said initial and duplicate colonies;

g) hybridizing the DNAs of the initial colonies on the one hand and the duplicate colonies on the other hand respectively with the abovesaid induced cDNA probes and non-induced cDNA probes (or conversely);

h) recovering DNAs of clones which hybridize with the induced cDNA probes and do not hybridize with the non-induced cDNA probes, whereby DNAs hybridizable with the mRNA capable of being translated into said inducible protein or polypeptide, particularly interferon, are obtained.

The process of the invention is preferably applied to the production of highly-purified mRNA of interferon of human origin.

It will be appreciated that some of the steps defined above need not be performed in the exact order which has been indicated hereabove. This applies particularly to step c) relating to the synthesis of the cDNA probes. In fact the latter step c)even needs not be a step of the process of the invention per se. Analogous probes, from other cellular sources may be used instead.

In a further advantageous embodiment of the invention, steps c)and d), as above defined, are carried out on fractions only of the mRNAs which can be extracted from cells, whether they have been "induced" or "non-induced". In that respect advantage can be taken of the fact that mRNAs comprise a poly-A portion which enables the separation of the mRNA from total RNA by binding to oligo-T-cellulose. The subsequently eluted mRNA fraction is advantageously subsequently fractionated by sucrose gradient centrifugation, the different bands being then separately translated into a suitable cell-free system, such as a reticulocyte lysate, each of the translation products being then tested for their capability of being immunoprecipitated by an anti-interferon serum. The bands of mRNA whose translation products gave a positive reaction in such immunoprecipitation test were then retained for carrying out the two above defined steps c) and d). A further aspect of this procedure is that two different mRNAs coding for interferon can be isolated from human fibroblastic cells if these cells are induced as in a) above. The smallest mRNA sediments at 11S and yields by translation in a cell-free system a protein of molecular weight 20,000 which is selectively precipitated by antibodies prepared against one of the interferons that can be purified from these cells. This protein is human interferon (IFN)-$\beta$1. The largest mRNA sediments at 14S and yields a protein of molecular weight 23,000 which is precipitated by antibodies against a less purified preparation of fibroblastic interferon. This protein is designated human interferon-$\beta$2. Fractions of mRNA for both proteins were used for step d) above. This makes possible to produce at will IFN-$\beta$1 or IFN-$\beta$2 in substantially pure form. Hybridization (steps c, d, e, f, g, and h defined hereabove) thus enable single colonies of *E. coli* containing one of two interferon cDNA IFN $\beta$1 or $\beta$2 to be exactly identified. Particularly, it will be appreciated that those colonies which hybridize only with "induced" cDNA probes and not with the "non-induced" cDNA probes can only consist of those which have incorporated a modified vector having the cDNA corresponding to the interferon mRNA, inasmuch as:

a) the said DNA, not being hybridizable with the "non-induced" cDNA probe, does not accordingly correspond to any of the mRNAs normally produced by a "non-induced" cell and b) the only difference between the two probes being used is that the "induced" cDNA probe differs only from the other one by the fact that it contains a cDNA derived from one of the interferon mRNA.

It will be obvious to the man skilled in the art that the forming of these cDNA probes can be achieved by any method known per se, particularly by transcription in the presence of a reverse transcriptase. It is of advantage to use a high producer bacterial-vector such as the pBR322 plasmid. In order to obtain the later expression in a microorganism of the vectors modified by the interferon cDNA, one may resort to a set of vectors as defined by Patrick Charney et al., in "Bacteriophage Lambda and Plasmid Vectors Allowing Fusion of Cloned Genes in each of the three translational phases". Nucleic Acids Res., 1978-5(12), 4 479–94.

According to a further important step Of the invention, the above modified vector, whichever be its translational phase, can be used for extracting interferon mRNA from the RNA mixture produced by "induced" cells, which process comprises contacting these RNAs with such a vector modified by the interferon cDNA previously immobilized on a support, under conditions suitable for causing hybridization and thereafter eluting the fixed mRNA from the immobilized DNA vector. In such a way, mRNA of human interferon (either IFN $\beta$1 or IFN $\beta$2) may be obtained in .highly purified form.

The high state of purification can be appreciated by the fact that the translation product, in a suitable in vitro system, consists in each case essentially of a single polypeptide compound having interferon activity, and which can be precipitated by said antibodies to human interferon.

The invention thus concerns also said purified mRNAs which comprises normally up to 900–1,000 nucleotides for IFN-$\beta$1 and 1,250–1,350 for IFN-$\beta$2. In the same manner it also concerns the corresponding cDNA which can be obtained by reverse transcription of said RNAs. The invention concerns also the existence of two different interferon mRNAs and hence protein moieties that may have also different biological importance. It goes without saying that each of the hybridization steps involved in the present application will be preceded, where appropriate, by a denaturation of the possible double-stranded nucleic acids to insure that no double-stranded nucleic acids (which could induce interferon activity in cells) remains in the purified mRNAs when these are used for the production, by translation thereof, of substantially pure protein having interferon activity in vitro.

DESCRIPTION OF THE PREFERRED EMBODIMENT

The invention will be further illustrated in a nonlimitative manner by the more detailed description of a preferred embodiment thereof, taking into account, the appropriate Figures and Table.

BRIEF DESCRIPTION OF THE FIGURES AND TABLE

In the enclosed figures.

Table 1 demonstrates that this mRNA, upon translation in *Xenopus laevis* oocytes, yields biologically active interferon which inhibits the growth of a virus in human cells.

a) Purification of Two Interferon mRNAs From Human Diploid Fibroblasts

RNA was extracted from monolayer cultures of the human fibroblast line FS11 (isolated at the Weizmann Institute of Science). These diploid cells grown from foreskin explants taken from a normal individual 8 days after birth, were selected among 15 separate isolates for their capacity to produce high titers of interferon. Alternatively cultures of a clone of human SV80 cells were used. The cultures in Eagle's minimal medium with 10% fetal calf serum were maintained in 2.2 liter glass roller bottles or 22×22 cm plastic trays in 5% $CO_2$, 95% air at 37° C. Three days after confluency, the cultures were induced to produce interferon by exposure to poly(rI):(rC) 100 μg/ml, and cycloheximide (which blocks the synthesis of proteins by the host) 50 μg/ml for 3.5 hours. Actinomycin D (which blocks the synthesis of cellular RNA) 1 μg/ml, was added and 1 hour later the cells were lysed with buffered Nonidet-P40 detergent and cytoplasmic RNA was extracted with a phenolcresol mixture as Kirby (1965). The mRNAs were isolated from total RNA, by bringing into play the fact that they contain Poly A, by binding to oligo-dT-cellulose. The mRNA fraction was subsequently fractionated by sucrose gradient centrifugation. The fractions containing interferon mRNA were identified by microinjection to Xenopus laevis cocytes according to Raj N. K. B and Pitha P. M. (Proc. Natl. Acad. Sci. U.S.A. 74, 1483–1487, 1977), and measuring 24–40 hours later the antiviral activity of the interferon released in the oocyte incubation medium. Antiviral activity was measured by exposing FS11 cells to dilutions of the oocyte medium, infecting said cells with vesicular stomatitis virus and observing inhibition of the cytopathic effect caused by the virus. Interferon titers were calculated by comparison to a known solution, according to the last effective dilution. The fractions containing interferon mRNA were also identified by translation in a reticulocyte lysate followed by immunoprecipitation of the product according to the method of Weissenbach et al., (Eur. J. Biochemistry 98, 1–8, 1979).

Figure 1A:
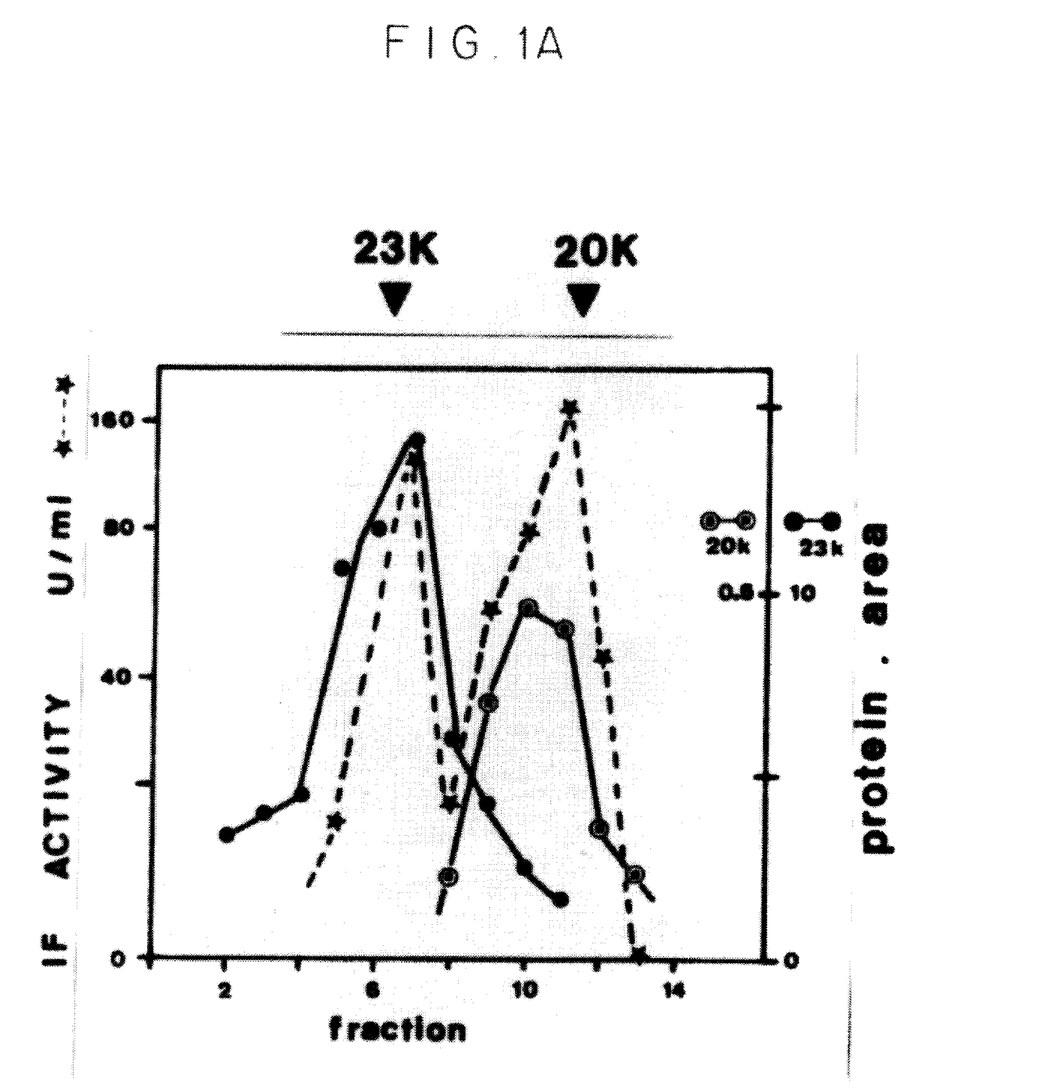
FIGS. 1A and 1B illustrate the fractionation of mRNA on a sucrose gradient and the translation of these mRNA fractions originating from induced cells to produce human interferon activity in *Xenopus laevis* oocytes and to produce specifically immunoprecipitated proteins in reticulocyte lysates, a process which separates the mRNA for IFN-$\beta$1 and IFN-$\beta$2.
Figure 1B:
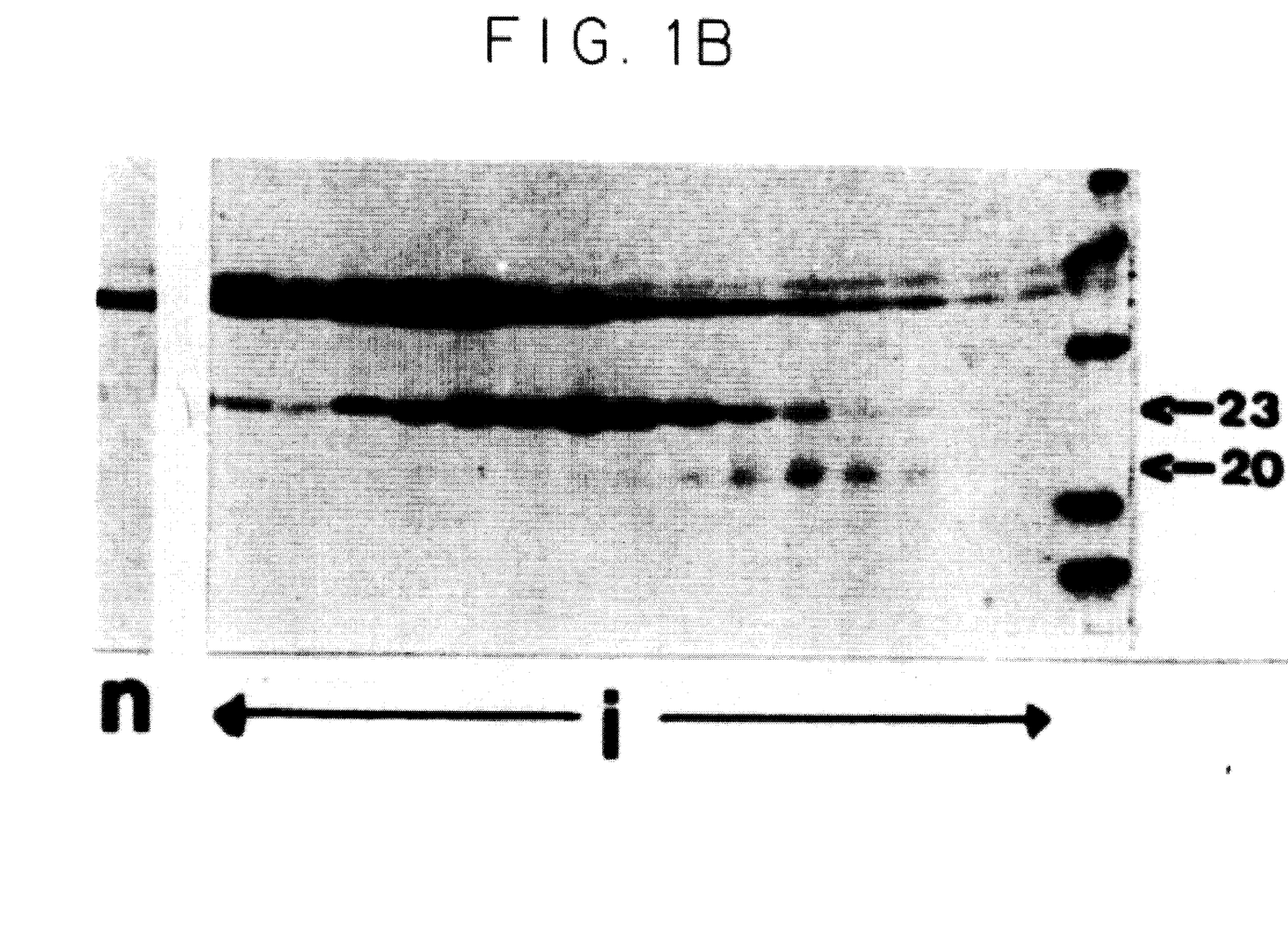

FIG. 1A shows the two peaks of interferon mRNA activity detected by injection to oocytes. FIG. 1B is representative of the immunoprecipitation lines obtained between the translation products and anti interferon serum, the two arrows showing the two polypeptides of molecular weight of 23,000 (23K) and 20,000 (20K). The sucrose gradient fractions coding for the 23K and 20K immunoprecipitated polypeptides are shown in FIG. 1A and can be seen to correspond to the two peaks of interferon mRNA activity. Interferon activity was also detected in the translation products of reticulocyte lysates by measuring induction of the (2'-5') oligoisoadenylate synthetase in human cells. By both methods it was seen that the largest interferon mRNA peak codes for the 23K polypeptide, while the smallest interferon mRNA peak codes for the 20K polypeptide. Both interferon mRNAs were in this way isolated and used for cloning in E. coli.

b) Cloning of Interferon β2 cDNA in E. coli

The purified mRNA from induced cells was calculated to contain about 1–3% of the mRNA for the 23,000 MW polypeptide and was used as template to synthesize cDNA with avian myeloblastosis virus, reverse transcriptase and oligo-dT as primer. After eliminating the RNA by alkali treatment, the second strand of DNA could be synthesized with reverse transcriptase or DNA polymerase I. Single-stranded DNA was cleaved off with nuclease S1, and the 3' ends of the DNA was elongated ("tailed") with nucleotide terminal transferase using dCTP as substrate. Plasmid pBR322 DNA was linearized with restriction endonuclease and was dG tailed with dGTP. The plasmid DNA was then hybridized with the dC-tailed human cDNA described above, and used to transfect E. coli DP50. Transfected bacterial colonies were identified by plating on agar plate containing Luria broth, diaminopimelic acid, thymidine and tetracycline. The colonies were further tested on similar agar plates but containing ampicillin as the only antibiotic. The ampicillin sensitive, tetracycline resistant bacterial colonies were grown on a nitrocellulose filter deposited on an agar plate as above with tetracycline 10 μg/ml. Over two thousands of the transformed colonies obtained were respectively transferred in part on other nitrocellulose filters, themselves on agar plates as hereabove indicated, each of the duplicate colonies being related (particularly by common numbering) to one of the initial colonies. After the colonies reached 3–5 mm in diameter, the filter (initial cultures and duplicates) were transferred on top of a stack of filter papers impregnated first with 0.5N NaOH, then with 0.15M NaCl and 0.1N NaOH to cause release in situ of their respective DNAs. The filters were neutralized and dried. To detect the bacterial colonies containing the interferon DNA sequences, the filters were hybridized with two different [$^{32}$P]cDNA probes. One cDNA probe was prepared by reverse transcriptase of the mRNA from the sucrose gradient fraction from induced cells (arrow 23K of FIG. 1). The second probe was prepared identically from the similar fraction of the non-induced cell preparation. Both cDNA probes were synthesized using the four highly radioactive [$^{32}$P]-deoxynucleoside triphosphates as substrates and fragmented calf thymus DNA as primers. Random representation of the mRNA sequences in the cDNA probes was thereby achieved. Hybridization was carried out at 62°–64° C. for 18 hours in 0.9M NaCl-0.09M Na citrate buffer pH 7.0, the initial colonies being hybridized with the cDNA probes of the induced cells and the duplicate colonies with the cDNA probes of the non-induced cells (or conversely) respectively. After extensive washing the filters were exposed to X-ray film and the bacterial colonies able to hybridize to the induced cDNA but not to non-induced cDNA were identified. In this manner 20 different bacterial colonies were isolated out of a total of over 2,000 transformed colonies screened. All of these 20 bacterial colonies contain multiple copies of a plasmid in which were inserted sequences of human mRNA expressed only after cells have been induced to produce interferon by poly (rI:rC).

Figure 2:
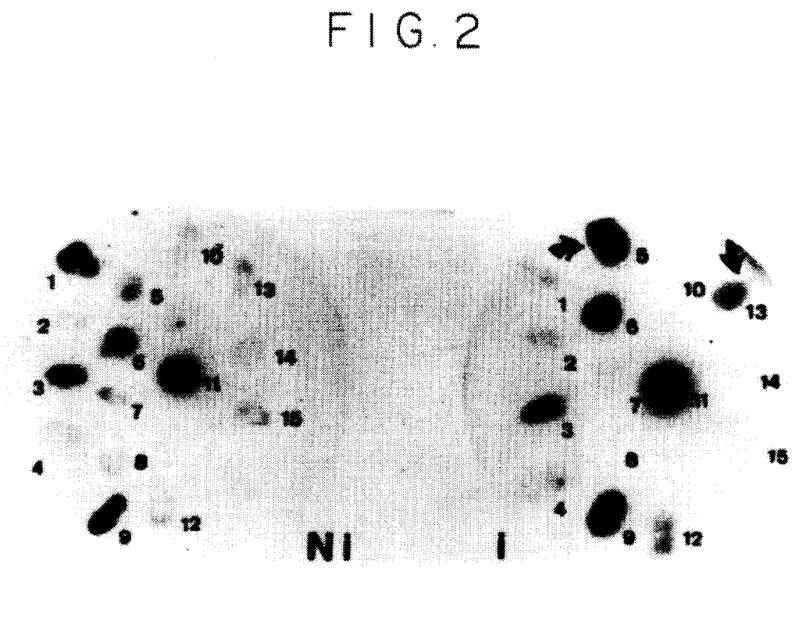
FIG. 2 illustrates the result of a differential hybridization procedure of the DNAs of the same bacterial colonies with the two above-mentioned probes from "induced" and "non-induced" cells, respectively.

An example illustrating this technique is shown in FIG. 2 in connection with fifteen pairs of alkali-treated pairs of colonies (initials and duplicates) on their nitrocellulose filters, whose DNA have been hybridized with [$^{32}$P]-cDNA prepared against mRNA fraction 23K of FIG. 1, from cells induced (i) or non-induced (n.i.) by poly(rI):(rC) for interferon production. Arrows show two colonies, particularly colonies numbered 5 and 13, which contain induced sequences. Colony number 13 was designated as E. coli DP50/A341. Clone A-341 was deposited on Jun. 2, 1992, at Collection Nationale de Cultures de Microorganismes, Institut Pasteur, 25, rue de Docteur Roux, 75724 Paris Cedex 15, France, and has been assigned depository accession number 1-1214.

c) Isolation of Interferon mRNA From Human Fibroblast

Figure 3:
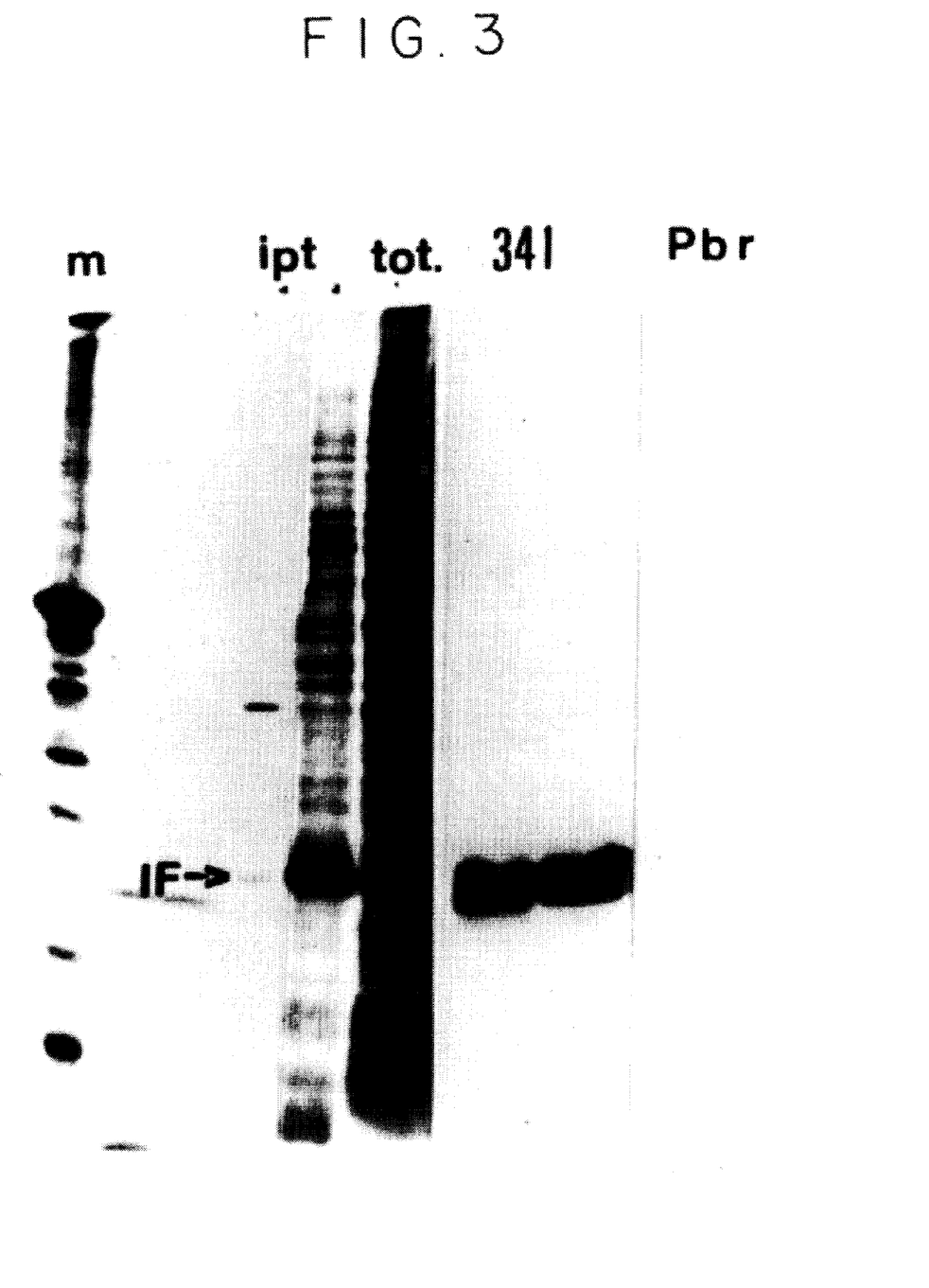
FIG. 3 illustrates a purification of interferon IFN-$\beta$2 mRNA by hybridization to immobilized DNA from bacterial clone A341 as demonstrated by translation in a reticulocyte lysate.

Isolation of interferon mRNA (and demonstration of the presence of interferon cDNA sequences in the plasmid DNA of clone A341) were obtained as follows: A 500 ml culture of this bacterial clone was used to prepare 50 μg plasmid DNA. This DNA (after previous denaturation) was covalently bound to diazobenzyloxymethyl cellulose powder according to the methods of Aldwine et al. (Proc. Natl. Acad. Sci. U.S.A. 1977, 74, 5350). In parallel, plasmid pBR322 DNA (not containing human DNA sequences) was similarly bound to cellulose. Poly A-containing mRNA, from human fibroblasts induced to produce interferon, was hybridized to the two DNA cellulose preparations in 50% formamide at 52° C. and eluted by raising the formamide concentration to 100% at 70° C. The RNA recovered after elution was translated in the reticulocyte cell-free system (FIG. 3). Whereby the essential translation product of the mRNA selected on the A341 DNA-cellulose was found to be essentially the 23,000 MW polypeptide. In contrast, no human interferon mRNA was recovered from the pBR322 DNA-cellulose. In comparison to the translation products of the human mRNA prior to hybridization to A341 DNA-cellulose it could be ascertained that the cloned A341 DNA is complementary to only little of the mRNA of the mixture. The product of the mRNA selected on A341 DNA-cellulose was immunoprecipitated by the anti-human fibroblast interferon serum (see FIG. 3).

The interferon mRNA could also be isolated by a similar procedure to that above but in which plasmid A341 DNA was bound to nitrocellulose filters, the RNA hybridized to it, and eluted by boiling for 1 min in $H_2O$.

The activity of this purified mRNA to code for biologically potent human interferon has shown by injection to Xenopus laevis oocyte followed by measuring the inhibition of virus multiplication in human cells exposed to the oocyte incubation medium (Table 1). The interferon activity of the purified β2 mRNA was also shown by the induction of (2'-5') oligo-isoadenylate synthetase in human cells by the oocyte translation products (Table 1).

Figure 4A:
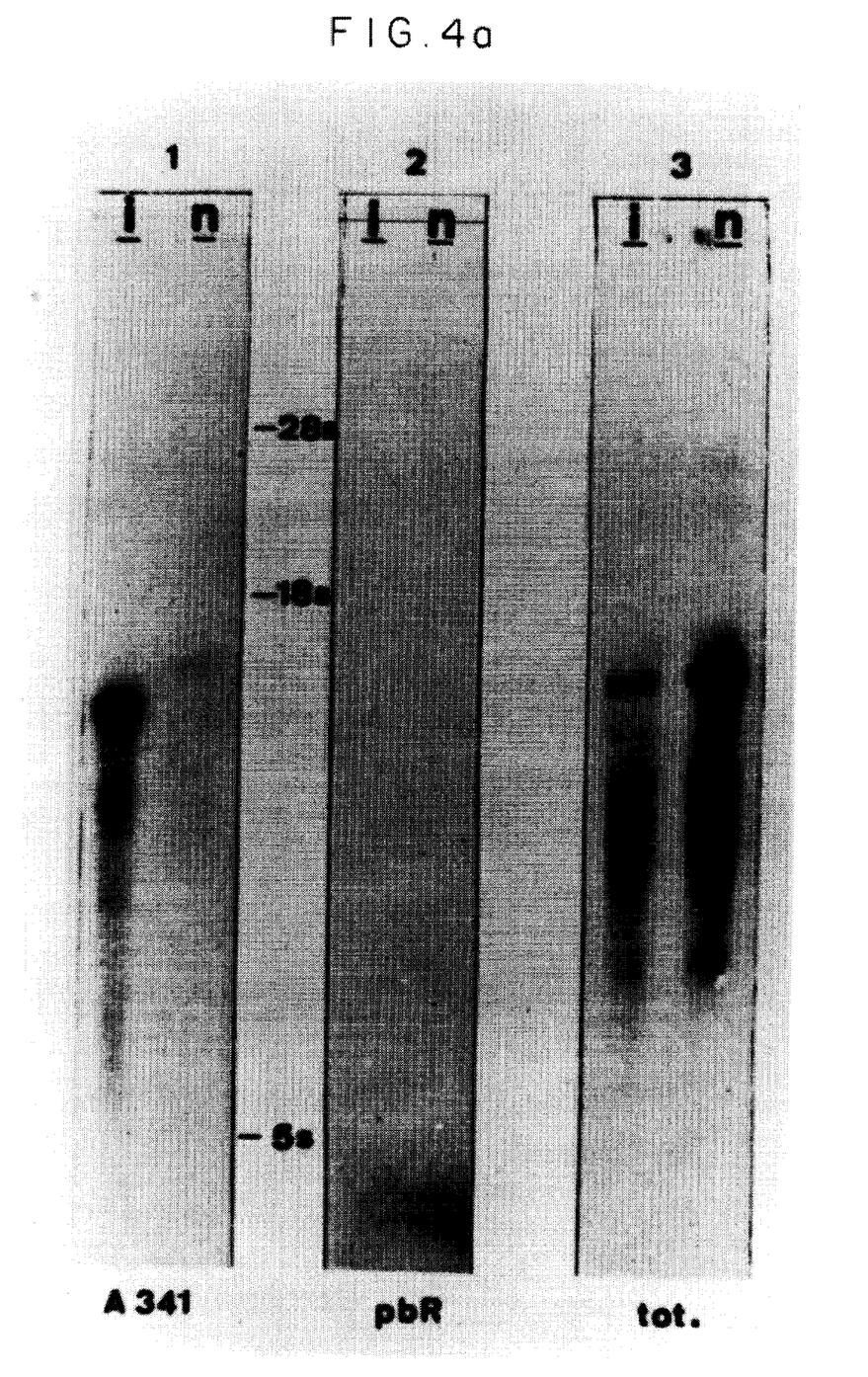
FIGS. 4*a* and 4*b* demonstrate that DNA from bacterial clone A341 is complementary to a 1,250–1,350long mRNA which appears in human cells only after induction of interferon synthesis.

Restriction enzyme mapping of A341 plasmid DNA showed that it contains a human DNA insert of about 900 nucleotides in the Pst site. The A341 DNA also hybridized to 3 fragments of the human genome digested by Eco R1 nuclease. These fragments are separated by agarose gel electrophoresis. Hybridization to agarose gel electrophoregrams of mRNA from human fibroblast further showed that A341 DNA is complementary to RNA sequences that are expressed only in cells exposed to the interferon inducer poly (rI:rC) (FIG. 4a). Even a one hour exposure of the cells to poly(rI:rC) leads to the accumulation of a 1,250–1,350 nucleotide long RNA hybridizing to A341 DNA, which represents IFN-β2 mRNA.

Figure 4B:
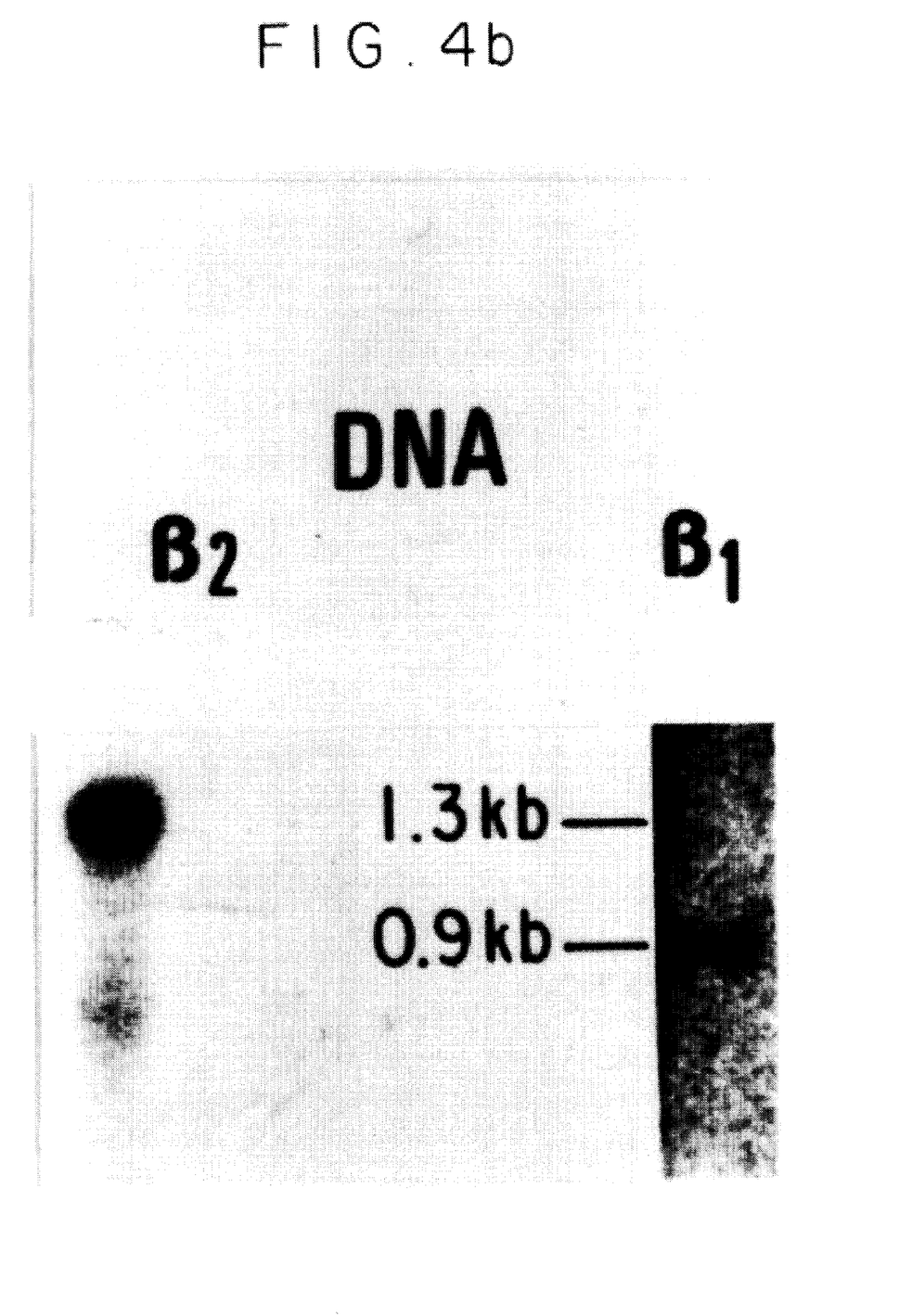

The above data demonstrated that the bacterial clone *E. coli* DP50/A341 contained in the Pst site of its pBR322 plasmid an insert of about 900 nucleotides of human cDNA sequences which are complementary to a human interferon mRNA. Several similarly prepared clones were obtained. FIG. 4b shows that clones for IFN-β2 hybridize to the largest 1,250–1,350 nucleotide long mRNA while clones for IFN-β1 hybridized to the smallest 900–1,000 nucleotide long mRNA.

The process can be used for obtaining clones of interferon DNA of different types (α, β, γ) from human cells.

Legends for Figures

FIGS. 1A and 1B: Sucrose gradient of poly $A^+$ RNA from human cells induced to produce interferon (1A). Sedimentation was from right to left. Ten Xenopus laevis oocytes were injected with 0.4 µg RNA of each fraction and after 40 hours, the medium around the oocytes was assayed on FS11 cells for interferon (left scale). Each RNA fraction (0.24 µg) was translated also in reticulocyte lysates and the $^{35}S$-methionine labeled products were precipitated with anti-interferon serum. The products analyzed by polyacrylamide gel electrophoresis are shown in lane i of (1B). Lane n in (1B) represents the immunoprecipitated products of unfractionated mRNA from non-induced cells. At the right end of (1B) are molecular weight markers (from top to bottom, 68, 46, 30, 18 and 14 daltons×$10^{-3}$). The position and intensity of the 23K and 20K protein (arrows) was recorded and is shown graphically in a (right scale).

The heaviest of the two interferon mRNAs is translated in the 23K protein while the smallest interferon mRNA is translated in the 20K protein.

FIG. 2: Detection of transformed bacterial clone containing interferon DNA. Fifteen alkali-treated colonies on nitrocellulose filters, were hybridized with [$^{32}P$]cDNA prepared against the 23K mRNA fraction (see FIG. 1) from cells induced (i) or non-induced (n.i.) by poly(rI):(rC) for interferon production. Arrows show two colonies which contain induced sequences. Colony number 13 is *E. coli* DP50/A341.

FIG. 3: Demonstration that clone *E. coli* DP50/A341 contains interferon DNA. Poly $A^+$ mRNA from human fibroblast induced for interferon production was hybridized to DNA from A341 plasmid covalently bound to cellulose and translated. Gel electrophoresis of the translation products show that mRNA which codes for the interferon (IF) polypeptide is uniquely selected from the mixture of total mRNAs. pBR DNA is unable to select this mRNA. Position of IF polypeptide is shown after immunoprecipitation with anti-interferon (ipt).

FIGS. 4a and 4b:

4a) Plasmid DNA of bacterial clone A341 hybridizes to a 14S (1,300 nucleotides long) mRNA found in cells induced for interferon production (i) but not in non-induced cells (n). Plasmid pBR DNA does not hybridize while uncloned total cDNA (tot) hybridizes to many mRNAs found also in non-induced cells. An agarose gel electrophoresis of the RNA followed by hybridization to the three $^{32}P$-DNAs is shown.

4b) Plasmid DNA from different clones of interferon DNA were used for a similar experiment of hybridization to mRNA electrophoregrams. Clones containing IFN-β2 DNA hybridize to the 1,300 nucleotide long mRNA, while clones with IFN-β1 DNA hybridize to the smaller 900 nucleotides long interferon mRNA.

TABLE 1

HYBRIDIZATION-TRANSLATION OF β2-INTERFERON mRNA

| Oocyte supernatant (diluted 1:10) | Expt. 1 V.S.V.-Virus Yield Radioimunoassay, cpm. | Expt. 2 Oligo-isoadenylate synthetase induction [$^{32}P$]-A2'p5'A, cpm Oocyte extract (diluted 1:1.5) | Calculated IF titer |
|---|---|---|---|
| uninjected | 7445 | 1700 | |
| with RNA hybridized to IF-β2 plasmid | 1920 | 4700 | 30 U/ml |
| with RNA hybridized to unrelated plasmid | 6015 | 1500 | 0 |
| Interferon standard 100 U/ml | 700 | 10,800 | |

*Clone E474 DNA was used in Expt. 1, and a pool of IF-β2 DNA plasmids for Expt. 2.

We claim:

1. A DNA which consists essentially of a DNA which codes for human fibroblast β-2 interferon polypeptide.

2. A vector which consists essentially of a vector containing genetic material including a nucleotide sequence translatable to a human fibroblast interferon-beta-2 polypeptide.

3. A heat cell which consists essentially of a cultivatable vector having a DNA insert which codes for a human fibroblast interferon-beta-2 polypeptide.

4. A vector which consists essentially of a vector containing a DNA molecule including a portion of the DNA which codes for interferon-beta-2, which DNA molecule is capable of hybridizing to mRNA encoding human interferon-beta-2 in 50% formamide at 52°.

5. A host cell which consists essentially of a cultivatable vector in accordance with claim 4.

6. A vector in accordance with claim 4, wherein said portion of the DNA which codes for interferon-beta-2 is that portion which is present in cDNA clone A341, CNCM Depository Accession No. 1-1214.

7. A host cell which consists essentially of a cultivatable vector in accordance with claim 6.

* * * * *

UNITED STATES PATENT AND TRADEMARK OFFICE
CERTIFICATE OF CORRECTION

PATENT NO. : 5,541,312
DATED : July 30, 1996
INVENTOR(S) : Revel et al

It is certified that error appears in the above-indentified patent and that said Letters Patent is hereby corrected as shown below:

Column 9:

Claim 3, line 1, delete "heat" and insert therefor --host--;

Column 10:

Claim 6, line 4, delete "1-1214" and insert therefor --I-1214--.

Signed and Sealed this

Fourth Day of February, 1997

Attest:

BRUCE LEHMAN

Attesting Officer

Commissioner of Patents and Trademarks

Disclaimer

5,541,312 — Michel Revel, Rehovot, Israel; Pierre Tiollais, Paris, France. PRODUCTION OF INTERFERON. Patent dated July 30, 1996. Disclaimer filed September 9, 2005, by the assignee, Yeda Research and Development Co., Ltd.

The term of this patent shall not extend beyond the expiration date of Patent No. 5,510,472.

*(Official Gazette, February 14, 2006)*

UNITED STATES PATENT AND TRADEMARK OFFICE
CERTIFICATE OF CORRECTION

| | | |
|---|---|---|
| PATENT NO. | : 5,541,312 | Page 1 of 1 |
| APPLICATION NO. | : 06/425934 | |
| DATED | : July 30, 1996 | |
| INVENTOR(S) | : Michel Revel and Pierre Tiollais | |

It is certified that error appears in the above-identified patent and that said Letters Patent is hereby corrected as shown below:

Title Page

Delete [45] and substitute "[45] Date of Patent: July 30, 1996*"

Insert after [73] -- * Notice:    This patent is subject to a corrected terminal disclaimer filed on September 9, 2005. --

Signed and Sealed this

Twenty-ninth Day of January, 2008

JON W. DUDAS
*Director of the United States Patent and Trademark Office*